United States Patent
Bandyopadhyay et al.

(10) Patent No.: US 10,743,821 B2
(45) Date of Patent: Aug. 18, 2020

(54) ANOMALY DETECTION BY SELF-LEARNING OF SENSOR SIGNALS

(71) Applicant: Tata Consultancy Services Limited, Mumbai (IN)

(72) Inventors: Soma Bandyopadhyay, Kolkata (IN); Arijit Ukil, Kolkata (IN); Rituraj Singh, Kolkata (IN); Chetanya Puri, Kolkata (IN); Arpan Pal, Kolkata (IN); C A Murthy, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 832 days.

(21) Appl. No.: 15/456,199

(22) Filed: Mar. 10, 2017

(65) Prior Publication Data

US 2018/0110471 A1 Apr. 26, 2018

(30) Foreign Application Priority Data

Oct. 21, 2016 (IN) .............................. 201621036139

(51) Int. Cl.
*G06N 3/08* (2006.01)
*G06F 11/22* (2006.01)
(Continued)

(52) U.S. Cl.
CPC ............ *A61B 5/7267* (2013.01); *A61B 5/021* (2013.01); *A61B 5/0468* (2013.01);
(Continued)

(58) Field of Classification Search
CPC ... A61B 5/021; A61B 5/0468; A61B 5/14551; A61B 5/7267; G06F 17/18; G06K 9/0053; G06N 20/00
(Continued)

(56) References Cited

U.S. PATENT DOCUMENTS 8,998,815 B2   4/2015 Venkatraman et al.
9,060,695 B2*  6/2015 Peters .................. A61B 5/0205
(Continued)

OTHER PUBLICATIONS

Sato, A. H., Ueda, M., & Munakata, T. (2004). Signal estimation and threshold optimization using an array of bithreshold elements. Physical Review E, 70(2), 021106. (Year: 2004).*
(Continued)

*Primary Examiner* — Brandon S Cole

(74) *Attorney, Agent, or Firm* — Finnegan, Henderson, Farabow, Garrett & Dunner LLP

(57) ABSTRACT

Accurate detection of anomaly in sensor signals is critical and can have an immense impact in the health care domain. Accordingly, identifying outliers or anomalies with reduced error and reduced resource usage is a challenge addressed by the present disclosure. Self-learning of normal signature of an input sensor signal is used to derive primary features based on valley and peak points of the sensor signals. A pattern is recognized by using discrete nature and strictly rising and falling edges of the input sensor signal. One or more defining features are identified from the derived features based on statistical properties and time and frequency domain properties of the input sensor signal. Based on the values of the defining features, clusters of varying density are identified for the input sensor signal and based on the density of the clusters, anomalous and non-anomalous portions of the input sensor signals are classified.

11 Claims, 6 Drawing Sheets

(51) Int. Cl.
*G06N 3/02* (2006.01)
*A61B 5/00* (2006.01)
*A61B 5/021* (2006.01)
*G06N 20/00* (2019.01)
*G06F 17/18* (2006.01)
*G06K 9/00* (2006.01)
*A61B 5/0468* (2006.01)
*A61B 5/1455* (2006.01)

(52) U.S. Cl.
CPC .......... *A61B 5/14551* (2013.01); *G06F 17/18* (2013.01); *G06K 9/0053* (2013.01); *G06N 20/00* (2019.01)

(58) Field of Classification Search
USPC ....................................................... 706/1–62
See application file for complete search history.

(56) References Cited

U.S. PATENT DOCUMENTS

| | | | | |
|---|---|---|---|---|
| 9,838,409 | B2* | 12/2017 | Flacher | H04L 63/1458 |
| 2004/0204865 | A1 | 10/2004 | Lee et al. | |
| 2009/0326349 | A1* | 12/2009 | McGonigle | A61B 5/14551 600/323 |
| 2011/0178967 | A1* | 7/2011 | Delp | G06F 11/2263 706/20 |
| 2014/0180730 | A1* | 6/2014 | Cordova | H04W 4/029 705/4 |
| 2014/0316292 | A1 | 10/2014 | McRae et al. | |
| 2015/0031965 | A1* | 1/2015 | Visvanathan | A61B 5/0059 600/301 |
| 2015/0245782 | A1* | 9/2015 | Morland | A61B 5/0095 600/301 |
| 2015/0341246 | A1* | 11/2015 | Boubez | H04L 41/0883 709/224 |
| 2015/0342478 | A1 | 12/2015 | Galen et al. | |
| 2016/0026915 | A1* | 1/2016 | Delp | G05B 23/0229 706/20 |
| 2017/0149810 | A1* | 5/2017 | Keshet | H04L 63/1425 |
| 2018/0110471 | A1* | 4/2018 | Bandyopadhyay | A61B 5/14551 |

OTHER PUBLICATIONS

Ben-David, S., Pál, D., & Simon, H. U. (Jun. 2007). Stability of k-means clustering. In International conference on computational learning theory (pp. 20-34). Springer, Berlin, Heidelberg. (Year: 2007).*

Park et al., "Arrhythmia detection from heartbeat using k-nearest neighbor classifier", Bioinformatics and Biomedicine (BIBM), 2013 IEEE International Conference on Bioinformatics and Biomedicine, IEEE, pp. 15-22, (2013) http://ieeexplore.ieee.org/document/6732594/.

Ghosal et al., "Classification of photoplethysmogram signal using self organizing map", 2015 IEEE International Conference on Research in Computational Intelligence and Communication Networks (ICRCICN), IEEE, pp. 114-118, (2015) http://ieeexplore.ieee.org/document/7434220/.

* cited by examiner

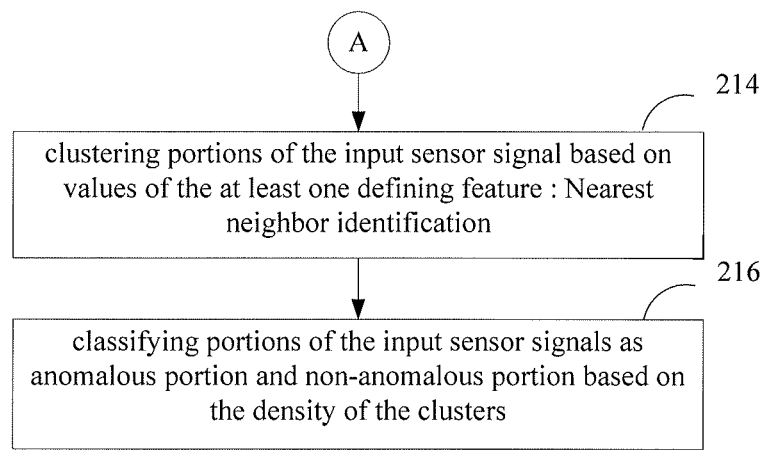
FIG.2 (contd.)

ANOMALY DETECTION BY SELF-LEARNING OF SENSOR SIGNALS

PRIORITY CLAIM

This U.S. patent application claims priority under 35 U.S.C. § 119 to: India Application No. 201621036139 filed on Oct. 21, 2016. The entire contents of the aforementioned application are incorporated herein by reference.

TECHNICAL FIELD

The embodiments herein generally relate to signal processing, and more particularly to systems and methods for anomaly detection by self-learning of sensor signals.

BACKGROUND

Sensor signals are gaining high importance for deriving parameters required to build smart applications based on sensor analytics. Hence extracting the various time series features of sensor signals and then co-relating them with application specific parameters is a necessity to obtain robust sensor analytics applications. However, sensor signals such as Photoplethysmograph (PPG) are characterized by a lot of noise and analytics generally run on low power/battery operated device like mobile phones. Therefore, identifying outlier/anomaly (with or without physiological abnormality) with reduced error and reduced resource usage is an important requirement.

SUMMARY

Embodiments of the present disclosure present technological improvements as solutions to one or more of the above-mentioned technical problems recognized by the inventors in conventional systems.

In an aspect, there is provided a processor implemented method comprising: deriving primary features associated with an input sensor signal based on the discrete nature of the input sensor signal, the primary features being minima points, maxima points, next minima points and three consecutive extrema points, wherein the input sensor signal comprises a non-anomalous portion thereof; detecting a pattern based on selective derived features obtained from the primary features; identifying at least one defining feature from the derived features based on statistical properties and time and frequency domain properties of the input sensor signal; performing self-learning of the input sensor signal based on the derived features and the at least one defining feature of the non-anomalous portion of the input sensor signal; clustering portions of the input sensor signal based on values of the at least one defining feature associated thereof into clusters of varying density; and classifying the portions of the input sensor signal as anomalous portions and non-anomalous portions based on the density of the clusters, wherein most dense clusters correspond to non-anomalous portions and least dense clusters correspond to anomalous portions of the input sensor signal.

In another aspect, there is provided a system comprising: one or more data storage devices operatively coupled to the one or more processors and configured to store instructions configured for execution by the one or more processors to: derive primary features associated with an input sensor signal based on the discrete nature of the input sensor signal, the primary features being minima points, maxima points, next minima points and three consecutive extrema points, wherein the input sensor signal comprises a non-anomalous portion thereof; detect a pattern based on selective derived features obtained from the primary features; identify at least one defining feature from the derived features based on statistical properties and time and frequency domain properties of the input sensor signal; perform self-learning the input sensor signal based on the derived features and the at least one defining feature of the non-anomalous portion of the input sensor signal; cluster portions of the input sensor signal based on values of the at least one defining feature associated thereof into clusters of varying density; and classify the portions of the input sensor signal as anomalous portions and non-anomalous portions based on the density of the clusters, wherein most dense clusters correspond to non-anomalous portions and least dense clusters correspond to anomalous portions of the input sensor signal.

In yet another aspect, there is provided a computer program product comprising a non-transitory computer readable medium having a computer readable program embodied therein, wherein the computer readable program, when executed on a computing device, causes the computing device to: derive primary features associated with an input sensor signal based on the discrete nature of the input sensor signal, the primary features being minima points, maxima points, next minima points and three consecutive extrema points, wherein the input sensor signal comprises a non-anomalous portion thereof; detect a pattern based on selective derived features obtained from the primary features; identify at least one defining feature from the derived features based on statistical properties and time and frequency domain properties of the input sensor signal; perform self-learning the input sensor signal based on the derived features and the at least one defining feature of the non-anomalous portion of the input sensor signal; cluster portions of the input sensor signal based on values of the at least one defining feature associated thereof into clusters of varying density; and classify the portions of the input sensor signal as anomalous portions and non-anomalous portions based on the density of the clusters, wherein most dense clusters correspond to non-anomalous portions and least dense clusters correspond to anomalous portions of the input sensor signal.

In an embodiment of the present disclosure, the derived features obtained from the primary features are (i) amplitude of maxima points, (ii) number of sampling points between two consecutive minima points, (iii) amplitude differences between minima points and next followed maxima points, (iv) number of sampling points between maxima points and next followed minima points and (v) consecutive amplitude and temporal differences of a number of sampling points in a pre-defined time frame detection window to identify the trend thereof.

In an embodiment of the present disclosure, the one or more hardware processors are further configured to represent the detected pattern in the form of a function of the derived features.

In an embodiment of the present disclosure, the one or more hardware processors are further configured to identify at least one defining feature by identifying at least one feature from the derived features satisfying conditions including: (i) difference between mean values of the derived features of non-anomalous portions of the input sensor signal and the mean values of the derived features of the input sensor signal is larger than at least a pre-defined first threshold, the pre-defined first threshold being based on the type of the input sensor signal; and (ii) standard deviation of the derived features of the non-anomalous portions of the input sensor signal is smaller than the standard deviation of the derived features of the input sensor signal by at least a pre-defined second threshold, the pre-defined second threshold being based on the type of the input sensor signal.

In an embodiment of the present disclosure, the one or more hardware processors are further configured to cluster portions of the input sensor signal based on values of the at least one defining feature associated thereof by k-means clustering method. Preferably, in accordance with the present disclosure, k=3.

In an embodiment of the present disclosure, the one or more hardware processors are further configured to cluster portions of the input sensor signal by merging of two or more clusters.

It is to be understood that both the foregoing general description and the following detailed description are exemplary and explanatory only and are not restrictive of the embodiments of the present disclosure, as claimed.

BRIEF DESCRIPTION OF THE DRAWINGS

The embodiments herein will be better understood from the following detailed description with reference to the drawings, in which.

Figure 1:
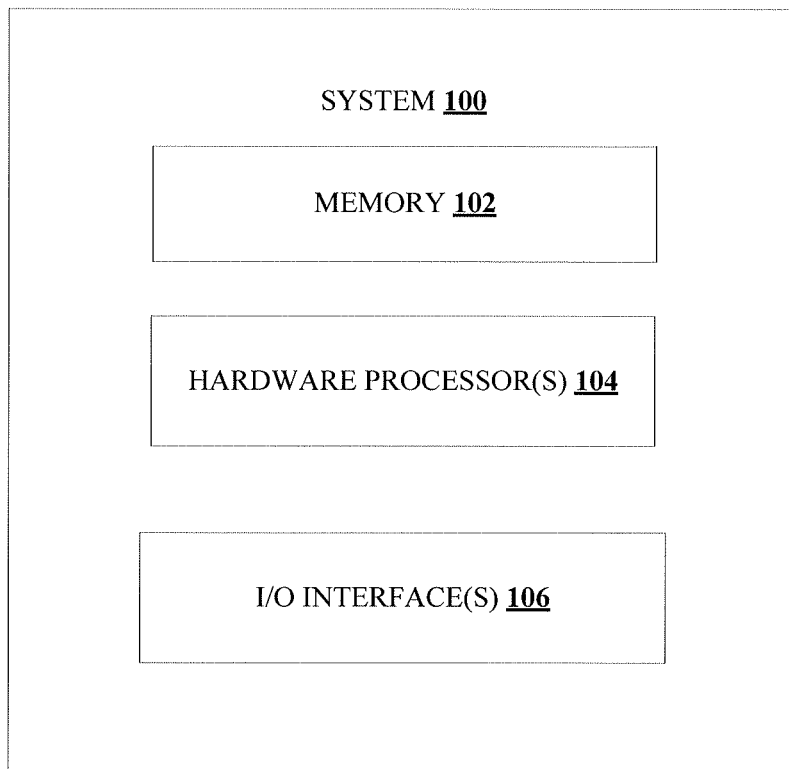
FIG. 1 illustrates an exemplary block diagram of a system for anomaly detection by self-learning of sensor signals, in accordance with an embodiment of the present disclosure.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Before setting forth the detailed explanation, it is noted that all of the discussion below, regardless of the particular implementation being described, is exemplary in nature, rather than limiting.

Detection of normal (non-anomalous) and anomalous events from sensor signals is a key necessity in today's smart world. In the context of the present disclosure, anomalous phenomena indicate outliers that may encompass noise, mainly due to motion artifacts and/or abnormalities. Identifying patterns from a sensor signal is a challenge specially without using training data. Conventional methods have used supervised learning to classify normal and anomalous phenomena. Systems and methods of the present disclosure provide semi-supervised means to classify normal and anomalous phenomena by using self-learning of signals, wherein as a first step in the analysis of sensor signals, a pattern of selective derived features is detected based on temporal and amplitude differences of primary features of sensor signals, the primary features being derived based on the peak and valley points of the sensor signals. Thus, in accordance with the present disclosure, the pattern of the sensor signal is learnt by applying the discrete nature of the sensor signals and basic definitions of minima and maxima. This is followed by identifying one or more defining features from the derived primary features based on statistical learning of normal signature of the sensor signals. Self-learning encompasses the dynamic variation in pattern recognition to classify anomalous phenomena. A clustering algorithm is then applied to cluster portions of the input sensor signal based on the values of the defining features associated with the portions of the input sensor signal; depending on the density of the clusters, the anomalous and non-anomalous portions of the sensor signals are then classified.

Referring now to the drawings, and more particularly to FIGS. 1 through 5, where similar reference characters denote corresponding features consistently throughout the figures, there are shown preferred embodiments and these embodiments are described in the context of the following exemplary system and method.

FIG. 1 illustrates an exemplary block diagram of a system 100 for anomaly detection by self-learning of sensor signals, in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
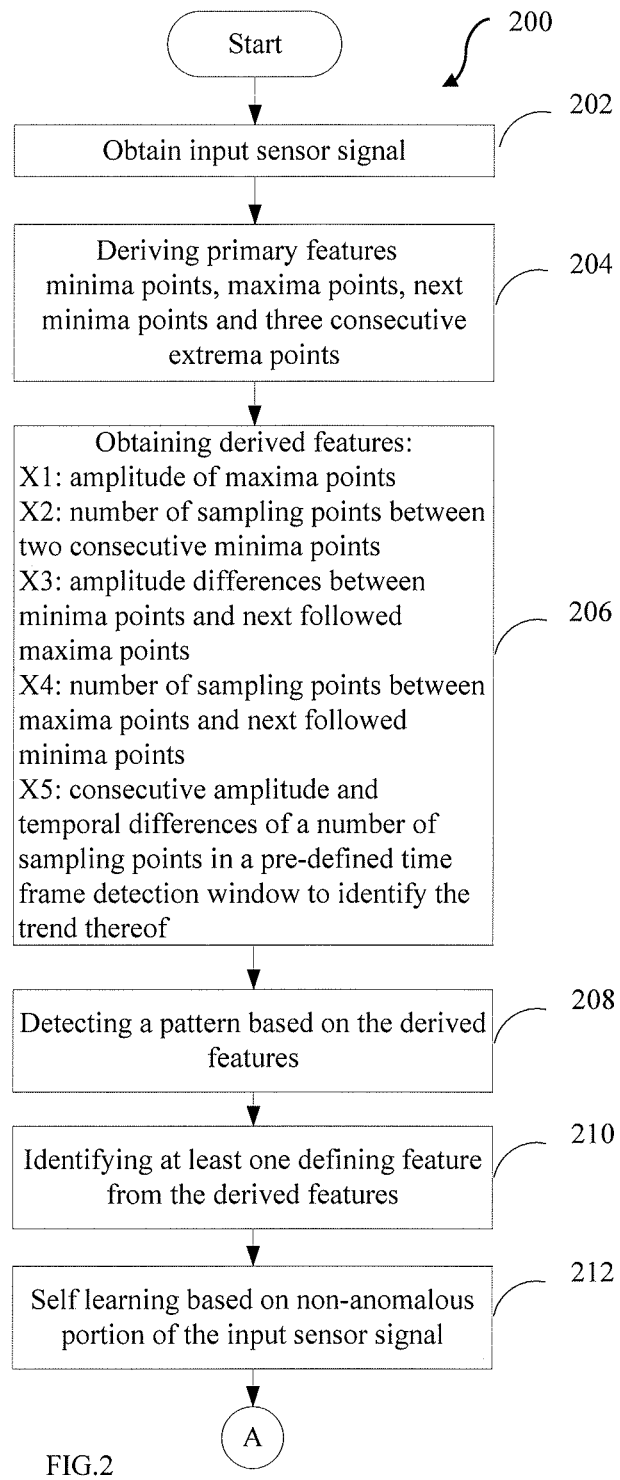
FIG. 2 illustrates an exemplary flow diagram of a method for anomaly detection by self-learning of sensor signals, in accordance with an embodiment of the present disclosure.

FIG. 2 illustrates an exemplary flow diagram of a method 200 for anomaly detection by self-learning of sensor signals, in accordance with an embodiment of the present disclosure. In an embodiment, the system 100 comprises one or more data storage devices or memory 102 operatively coupled to the one or more processors 104 and is configured to store instructions configured for execution of steps of the method 200 by the one or more processors 104.

In an embodiment, at step 202, the one or more processors 104 may obtain an input sensor signal wherein at least a portion of the input sensor signal is non-anomalous (normal signature) and may be used for self-learning at step 212. Accordingly a window of the normal signature of input sensor signal based on ground truth may be provided as an input to the system 100 for learning primary features associated with peak and valley points of the input sensor signal. Following the discrete nature of the input sensor signal, at step 204, the one or more processors 104 may derive the primary features associated with the input sensor signal including minima points, maxima points, next minima points and three consecutive extrema points. In accordance with the present disclosure, selective features from the primary features are derived at step 206 for detecting a pattern associated with the input sensor signal at step 208. In an embodiment, the derived features include:
(i) X1=amplitude of maxima points,
(ii) X2=number of sampling points between two consecutive minima points,
(iii) X3=amplitude differences between minima points and next followed maxima points,
(iv) X4=number of sampling points between maxima points and next followed minima points and
(v) X5=consecutive amplitude and temporal differences of a number of sampling points in a pre-defined time frame detection window to identify trends among them.

In the context of the present disclosure, the detection window may be a 300 millisecond window.

In an embodiment, the step of detecting a pattern based on selective derived features may further comprise representing the detected pattern in the form of a function of the derived features. For instance, Pattern=f(X1, X2, X3, X4, X5)

In an embodiment, a semi-supervised approach is used to identify, at step 210, at least one defining feature from the derived features based on statistical properties and time and frequency domain properties of the input sensor signal. For each of the derived features of each of the input sensor signal, mean ($\mu$) and standard deviation ($\sigma$) is computed for the normal signature or non-anomalous portion of the input sensor signal. The one or more defining features are those derived features that satisfy the following two conditions—
(i) difference between mean values of the derived features of non-anomalous portions of the input sensor signal and the mean values of the derived features of the input sensor signal is significantly large; in an embodiment the difference is larger than at least a pre-defined first threshold, the pre-defined first threshold being based on the type of the input sensor signal; and
(ii) standard deviation of the derived features of the non-anomalous portions of the input sensor signal is significantly smaller than the standard deviation of the derived features of the input sensor signal; in an embodiment the standard deviation of the derived features of the non-anomalous portions of the input sensor signal is smaller than the standard deviation of the derived features by at least a pre-defined second threshold, the pre-defined second threshold being based on the type of the input sensor signal.

In an embodiment, the pre-defined first threshold and the pre-defined second threshold may have same values.
The aforementioned two conditions may be further understood from the description of Table 1 and Table 2 herein below.

Once the self-learning process, at step 212, based on the non-anomalous portion of the input sensor signal is completed, the one or more processors 104 may cluster, at step 214, portions of the input sensor signal based on values of the at least one defining feature associated with the input sensor signal into clusters of varying density. In an embodiment, the step of clustering portions of the input sensor signal is based on k-means clustering method. In a preferred embodiment of the present disclosure, the step of clustering portions of the input sensor signal is based on 3-means clustering method with k=3. In an embodiment, the step of clustering comprises merging of two or more of the clusters. For instance, lower density clusters having insignificant members in comparison to dense clusters may be merged to detect anomalous portions of the input sensor signal. In an embodiment, along with the density of the clusters, the nearness among the cluster's centroids may also be taken into account, if necessary for merging.

In an embodiment, at step 216, the one or more processors 104 may classify portions of the input sensor signal as anomalous portions and non-anomalous portions based on the density of the clusters. In an embodiment, most dense clusters may be classified as corresponding to non-anomalous portions and least dense clusters may be classified as corresponding to anomalous portions of the input sensor signal. In accordance with the present disclosure, it is presumed that percentage of normal part of the input sensor signal is more than that of the anomalous part. Classification of normal and anomalous portions is based on ground truth. Systems and methods of the present disclosure thus enable automating anomaly detection for any sensor signal as compared to prior art wherein domain specific features are considered and anomaly detection relies on supervised learning.

Figure 3:
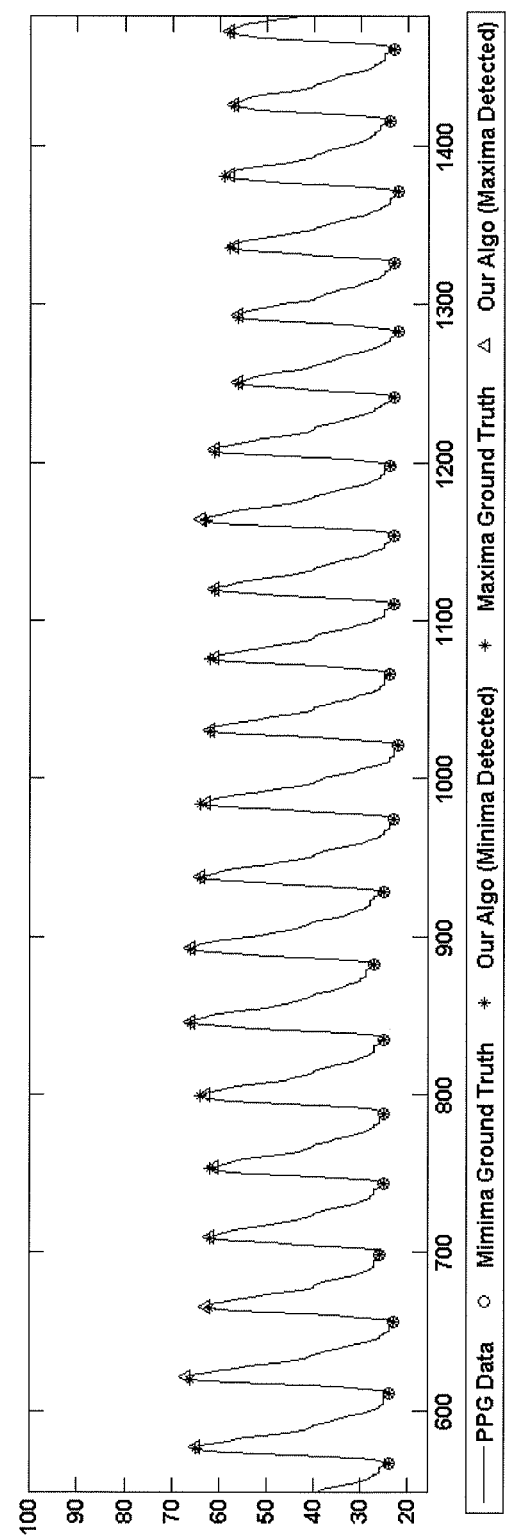
FIG. 3 illustrates an exemplary graphical illustration of maxima and minima points detected as part of self-learning of an input sensor signal, in accordance with an embodiment of the present disclosure.
Figure 4:
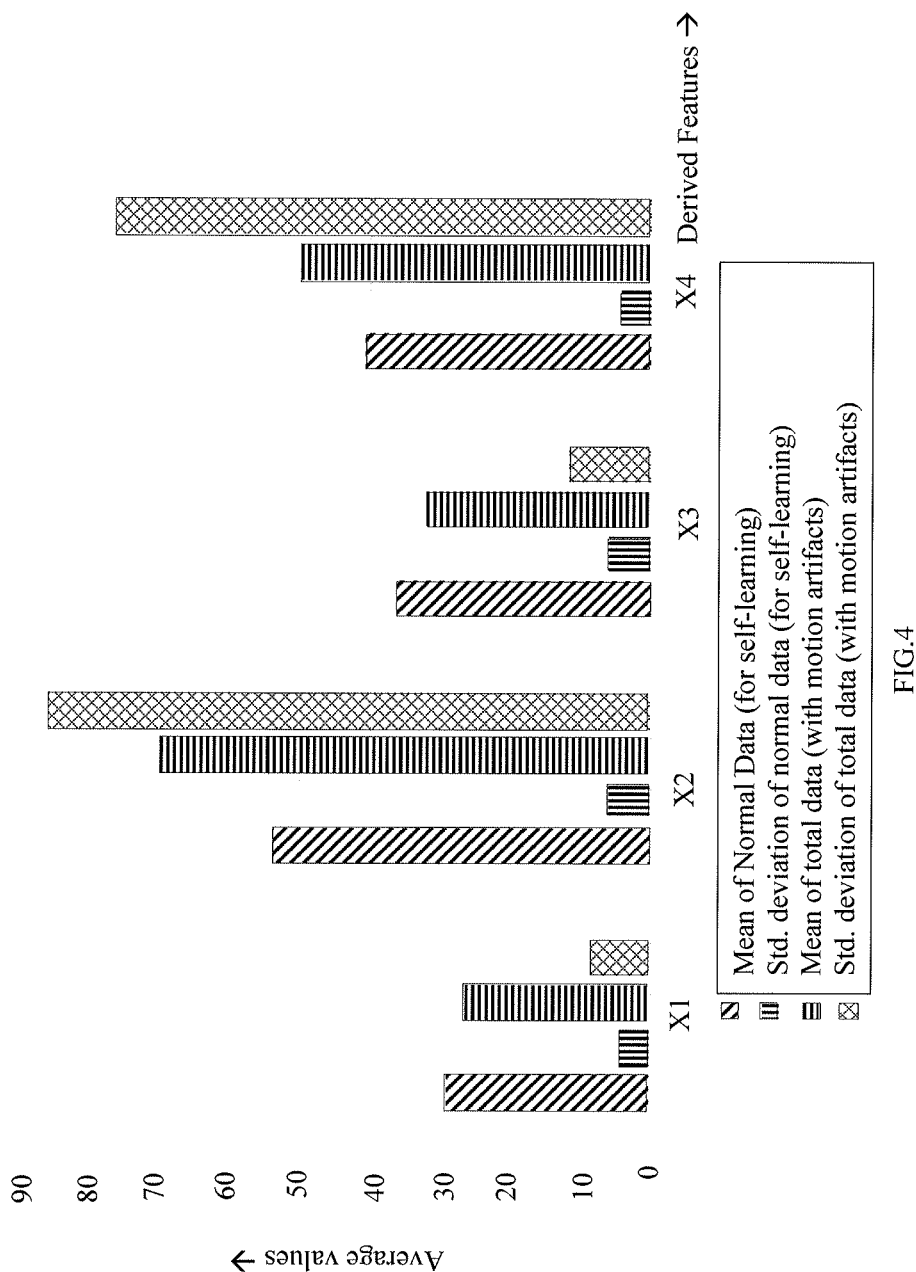
FIG. 4 illustrates an exemplary graphical illustration of comparative statistical properties and time and frequency domain properties of an input sensor signal, in accordance with an embodiment of the present disclosure.

Empirical Evaluation: Fingertip PPG data was collected from persons in the age group 20 to 50 years. Total duration of the collected data was 5 minutes with 30 seconds normal and 10 seconds motion artifacts where the persons moved their finger multiple times. The system of the present disclosure used a sample of normal non-noisy data (30 seconds) for self-learning. During the self-learning phase, the system of the present disclosure derives maxima and minima by following strictly rising and falling edges and the discrete nature of the signal. For instance, minima points are detected as follows:

$$\tilde{x}_{k-\frac{T2}{2}} > \tilde{x}_{k-\frac{T2}{2}+1} \ldots > \tilde{x}_{k-1} > \tilde{x}_k < \tilde{x}_{k+1} \ldots < \tilde{x}_{k+\frac{T2}{2}}$$

wherein, T2 is a detection window of 300 milliseconds, x̃ is a smoothened signal applying moving average technique. FIG. 3 illustrates an exemplary graphical illustration of maxima and minima points detected as part of self-learning of an input sensor signal, in accordance with an embodiment of the present disclosure. After detecting the minima and maxima points, the system of the present disclosure discovers pattern of the normal (non-anomalous) portion as well as complete signal by deriving X1, X2, X3 and X4 and is followed by selection of the defining feature. Illustrations of means and standard deviations are shown in Table 1, Table 2 whereas FIG. (corresponding to Table 1) illustrates an exemplary graphical illustration of comparative statistical properties and time and frequency domain properties of the input sensor signal, in accordance with an embodiment of the present disclosure. Particularly, FIG. 4 illustrates the average of X1, X2, X3 and X4 for 9 signals collected for the evaluation.

TABLE 1

Statistical deviations of different features for an exemplary signal 1

| Derived features | Data: Non-anomalous (Normal) portion of the input sensor signal | | Data: Complete input sensor signal | |
|---|---|---|---|---|
| | (μ) | (σ) | (μ) | (σ) |
| X1 | 60.66667 | 2.216819 | 66.71631 | 16.09806 |
| X2 | 48.00 | 1.75662 | 45.32624 | 17.62121 |
| X3 | 36.11111 | 2.561002 | 48.19149 | 17.36454 |
| X4 | 34.91667 | 1.5 | 28.15603 | 10.68797 |

TABLE 2

Statistical deviations of different features for an exemplary signal 2

| Derived features | Data: Non-anomalous (Normal) portion of the input sensor signal | | Data: Complete input sensor signal | | Difference Between Mean (Data: Normal − Data: Complete) | Difference Between Std. Deviation (Data: Normal − Data: Complete) |
|---|---|---|---|---|---|---|
| | (μ) | (σ) | (μ) | (σ) | | |
| X1 | 3.45757 | 0.080815 | 3.297586 | 0.384283 | 0.159984361 | 0.303468717 |
| X2 | 100.5714 | 6.925148 | 97.07075 | 28.87905 | 3.500673854 | 21.95390534 |
| X3 | 1.859346 | 0.15215 | 1.511768 | 0.591044 | 0.347577673 | 0.438893477 |
| X4 | 71.89286 | 6.154428 | 64.87264 | 23.42813 | 7.020215633 | 17.27370377 |

Figure 5:
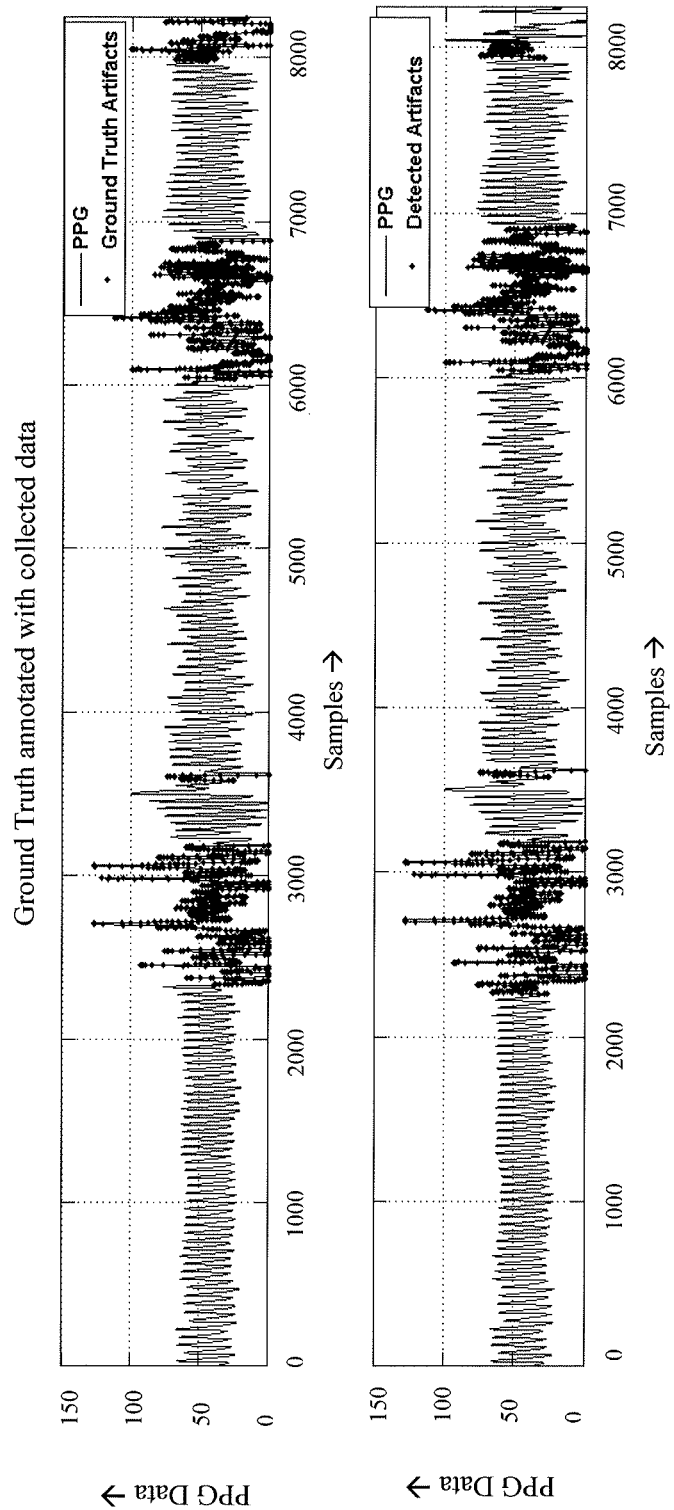
FIG. 5 illustrates a graphical representation of anomaly detected in accordance with the present disclosure as compared with ground truth data.

It may be noted from Table 2 that for each of X2 and X4, the difference between mean values of normal and the complete portion of the signal is significantly large (3.5 and 7.02 for X2 and X4 respectively), and the standard deviation for the normal part is significantly smaller than that of the complete signal (with a difference of 21.95 and 17.27 for X2 and X4 respectively). In the context of this example, the pre-defined first threshold may have been set as say 2; wherein both X2 and X4 having difference between mean values of normal and the complete portion of the signal as 3.5 and 7.02 respectively qualify as defining features. Also, the pre-defined second threshold may have been set as say 15; wherein both X2 and X4 having a difference of 21.95 and 17.27 qualify as defining features. Therefore, X2 and X4 in the data under consideration satisfy the two conditions required to qualify as the defining features of the method present disclosure. Clustering is performed using X2 and X4 with the help of k-means algorithm with k=3, where the dense cluster indicates the normal phenomenon and least dense cluster indicates anomalous phenomenon. Lower density clusters were merged (having insignificant members in comparison to the dense cluster) to detect the anomalous samples of the signal. The detected anomaly was compared with ground truth to assess the performance of the system and method of the present disclosure. FIG. 5 illustrates a graphical representation of anomaly detected in accordance with the present disclosure as compared with ground truth data.

TABLE 3 performance measure of the detected anomaly for the exemplary signal 1

| Performance (%) | Anomalous subsequence detection |
|---|---|
| Precision | 90.27 |
| Sensitivity | 92.09 |

From the above described empirical evaluation using real field quasi-periodic photoplethysmogram (PPG) signal with (or without) motion artifacts, it may be noted that 90% accuracy was achieved in detecting anomalous phenomena in the signal by the system and method of the present disclosure. PPG signals have an immense impact on cardiac health monitoring, stress, blood pressure, and SPO2 (saturation of peripheral oxygen) measurement. Accordingly, systems and methods of the present disclosure can have several applications particularly in the healthcare domain.

The written description describes the subject matter herein to enable any person skilled in the art to make and use the embodiments of the present disclosure. The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments of the present disclosure may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules comprising the system of the present disclosure and described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The various modules described herein may be implemented as software and/or hardware modules and may be stored in any type of non-transitory computer readable medium or other storage device. Some non-limiting examples of non-transitory computer-readable media include CDs, DVDs, BLU-RAY, flash memory, and hard disk drives.

Further, although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope and spirit of disclosed embodiments being indicated by the following claims.

What is claimed is:

1. A processor implemented method (200) for anomaly detection in an input sensor signal, comprising:
    deriving primary features associated with the input sensor signal based on discrete nature of the input sensor signal, the primary features being minima points, maxima points, next minima points and three consecutive extrema points (204), wherein the input sensor signal comprises a non-anomalous portion thereof;
    detecting a pattern associated with the input sensor signal based on selective derived features obtained from the primary features (206, 208) and representing the detected pattern in the form of a function of the derived features;
    identifying, using a semi-supervised approach, at least one defining feature from the derived features based on statistical properties and time and frequency domain properties of the input sensor signal (210), wherein the identified defining features are the derived features that satisfy conditions including:
        (i) difference between mean values of the derived features of the non-anomalous portion of the input sensor signal and the mean values of the derived features of complete portion of the input sensor signal is larger than at least a pre-defined first threshold, the pre-defined first threshold being based on the type of the input sensor signal; and
        (ii) standard deviation of the derived features of the non-anomalous portion of the input sensor signal is smaller than the standard deviation of the derived features of complete portion of the input sensor signal by at least a pre-defined second threshold, the pre-defined second threshold being based on the type of the input sensor signal;
    performing self-learning of the input sensor signal based on the derived features and the at least one defining feature of the non-anomalous portion of the input sensor signal (212);
    clustering portions of the input sensor signal based on values of the at least one defining feature associated thereof into clusters of varying density (214); and
    automatically classifying the portions of the input sensor signal as anomalous portions and non-anomalous portions based on the density of the clusters (216) and ground truth, wherein most dense clusters correspond to non-anomalous portions and least dense clusters correspond to anomalous portions of the input sensor signal,
    wherein self-learning of the input sensor signal encompasses dynamic variation in pattern recognition to classify the anomalous portions and non-anomalous portions.

2. The processor implemented method of claim 1, wherein the derived features obtained from the primary features are (i) amplitude of maxima points, (ii) number of sampling points between two consecutive minima points, (iii) amplitude differences between minima points and next followed maxima points, (iv) number of sampling points between maxima points and next followed minima points and (v) consecutive amplitude and temporal differences of a number of sampling points in a pre-defined time frame detection window to identify trends thereof.

3. The processor implemented method of claim 1, wherein the step of clustering portions of the input sensor signal based on values of the at least one defining feature associated thereof is based on k-means clustering method.

4. The processor implemented method of claim 3, wherein the step of clustering portions of the input sensor signal is based on 3-means clustering method with k=3.

5. The processor implemented method of claim 1, wherein the step of clustering comprises merging of two or more of the clusters.

6. A system (100) for anomaly detection in an input sensor signal, comprising:
one or more data storage devices (102) operatively coupled to one or more hardware processors (104) and configured to store instructions configured for execution by the one or more hardware processors to:
derive primary features associated with the input sensor signal based on discrete nature of the input sensor signal, the primary features being minima points, maxima points, next minima points and three consecutive extrema points, wherein the input sensor signal comprises a non-anomalous portion thereof;
detect a pattern associated with the input sensor signal based on selective derived features obtained from the primary features) and represent the detected pattern in the form of a function of the derived features;
identify, using a semi-supervised approach, at least one defining feature from the derived features based on statistical properties and time and frequency domain properties of the input sensor signal, wherein the identified defining features are the derived features that satisfy conditions including:
(i) difference between mean values of the derived features of the non-anomalous portion of the input sensor signal and the mean values of the derived features of complete portion of the input sensor signal is larger than at least a pre-defined first threshold, the pre-defined first threshold being based on the type of the input sensor signal; and
(ii) standard deviation of the derived features of the non-anomalous portion of the input sensor signal is smaller than the standard deviation of the derived features of complete portion of the input sensor signal by at least a pre-defined second threshold, the pre-defined second threshold being based on the type of the input sensor signal;
perform self-learning the input sensor signal based on the derived features and the at least one defining feature of the non-anomalous portion of the input sensor signal;
cluster portions of the input sensor signal based on values of the at least one defining feature associated thereof into clusters of varying density; and
classify automatically, the portions of the input sensor signal as anomalous portions and non-anomalous portions based on the density of the clusters and ground truth, wherein most dense clusters correspond to non-anomalous portions and least dense clusters correspond to anomalous portions of the input sensor signal,
wherein self-learning of the input sensor signal encompasses dynamic variation in pattern recognition to classify the anomalous portions and non-anomalous portions.

7. The system of claim 6, wherein the derived features obtained from the primary features are (i) amplitude of maxima points, (ii) number of sampling points between two consecutive minima points, (iii) amplitude differences between minima points and next followed maxima points, (iv) number of sampling points between maxima points and next followed minima points and (v) consecutive amplitude and temporal differences of a number of sampling points in a pre-defined time frame detection window to identify the trend thereof.

8. The system of claim 6, wherein the one or more hardware processors are further configured to cluster portions of the input sensor signal based on the values of the at least one defining feature associated thereof based on k-means clustering method.

9. The system of claim 8, wherein the one or more hardware processors are further configured to cluster portions of the input sensor signal based on 3-means clustering method with k=3.

10. The system of claim 6, wherein the one or more hardware processors are further configured to cluster portions of the input sensor signal by merging of two or more clusters.

11. A computer program product comprising a non-transitory computer readable medium having a computer readable program embodied therein, wherein the computer readable program, when executed on a computing device, causes the computing device to:
derive primary features associated with an input sensor signal based on the discrete nature of the input sensor signal, the primary features being minima points, maxima points, next minima points and three consecutive extrema points, wherein the input sensor signal comprises a non-anomalous portion thereof;
detect a pattern associated with the input sensor signal based on selective derived features obtained from the primary features and represent the detected pattern in the form of a function of the derived features;
identify, using a semi-supervised approach, at least one defining feature from the derived features based on statistical properties and time and frequency domain properties of the input sensor signal, wherein the identified defining features are the derived features that satisfy conditions including:
(i) difference between mean values of the derived features of the non-anomalous portion of the input sensor signal and the mean values of the derived features of complete portion of the input sensor signal is larger than at least a pre-defined first threshold, the pre-defined first threshold being based on the type of the input sensor signal; and
(ii) standard deviation of the derived features of the non-anomalous portion of the input sensor signal is smaller than the standard deviation of the derived features of complete portion of the input sensor signal by at least a pre-defined second threshold, the pre-defined second threshold being based on the type of the input sensor signal;
perform self-learning of the input sensor signal based on the derived features and the at least one defining feature of the non-anomalous portion of the input sensor signal;
cluster portions of the input sensor signal based on values of the at least one defining feature associated thereof into clusters of varying density; and
classify automatically, the portions of the input sensor signal as anomalous portions and non-anomalous portions based on the density of the clusters and ground truth, wherein most dense clusters correspond to non-anomalous portions and least dense clusters correspond to anomalous portions of the input sensor signal,
wherein self-learning of the input sensor signal encompasses dynamic variation in pattern recognition to classify the anomalous portions and non-anomalous portions.

* * * * *